United States Patent [19]
Jamroz et al.

[11] Patent Number: 5,406,378
[45] Date of Patent: Apr. 11, 1995

[54] METHOD AND APPARATUS FOR NON-CONTACT AND RAPID IDENTIFICATION OF WOOD SPECIES

[75] Inventors: Wes R. Jamroz, Montreal; Julien Tremblay, Dollard Des Ormeaux; Brian Wong, Montreal, all of Canada

[73] Assignee: MPB Technologies Inc., Dorval, Canada

[21] Appl. No.: 875,480

[22] Filed: Apr. 29, 1992

[51] Int. Cl.$^6$ ............................................. G01N 21/55
[52] U.S. Cl. .................................... 356/445; 356/432; 356/448
[58] Field of Search ............ 356/445, 446, 448, 432 T

[56] References Cited

U.S. PATENT DOCUMENTS

| | | |
|---|---|---|
| 3,693,079 | 9/1972 | Walker . |
| 4,082,950 | 4/1978 | Chen ................................. 250/343 |
| 4,171,918 | 10/1979 | Mactaggart ........................ 356/408 |
| 4,463,261 | 7/1984 | Bowman ............................ 250/339 |
| 4,540,285 | 9/1985 | Amer ............................. 356/432 T |
| 4,612,802 | 9/1986 | Clarke et al. ............................ 73/73 |
| 4,636,088 | 1/1987 | Rosencwaig et al. ........... 356/432 T |
| 4,752,689 | 6/1988 | Satake ................................ 250/339 |
| 4,785,185 | 11/1988 | Izatt et al. ...................... 250/339 X |
| 4,806,764 | 2/1989 | Satake ................................ 250/339 |
| 4,837,438 | 6/1989 | Sturm ................................ 250/339 |

Primary Examiner—Vincent P. McGraw
Attorney, Agent, or Firm—Jacobson, Price, Holman & Stern

[57] ABSTRACT

A method and apparatus for non-contact and rapid identification of wood species is provided. The method comprises irradiation of a substance with infra-red radiation which is intense enough to introduce microstructural modifications of the substance surface. Various wood species are identified by analyzing intensity of optical radiation which is scattered from the modified surface. The surface is irradiated with two (2) infra-red beams of different level of energy density. A wood sample is analyzed with optical beams: the first optical scanning is done prior to the first infra-red irradiation; the second optical scanning is done after the first infra-red irradiation; the third optical scanning is done after the second infra-red irradiation. It has been determined experimentally, that various wood species can be identified by analyzing intensities of the optical beams scattered from the modified surface. The method allows for non-contact, rapid and in-line identification of various species of wood. Also, it has been found, that the invented method allows for simultaneous determination of the moisture content. In one embodiment, the apparatus includes a source of optical radiation, an infra-red radiation source with adjustable energy densities, and a detector. The arrangement of optical axes of the detector and the radiation sources is such that they converge at the substance surface. In second embodiment, the apparatus includes two (2) sources of optical radiation, two (2) detectors, and an infra-red radiation source with adjustable energy densities. The arrangement of optical axes of the sources and detectors is such, that they are in line with the respect to the direction in which a substance is being moved.

15 Claims, 8 Drawing Sheets

METHOD AND APPARATUS FOR NON-CONTACT AND RAPID IDENTIFICATION OF WOOD SPECIES

FIELD OF THE INVENTION

This invention concerns a method and apparatus for in-line identification of various wood species. The common method of species identification is based on visual analysis of grain and fibre morphology of samples. More precise identification may require chemical and microscopic analysis or mass spectroscopy measurements. These methods either are limited to stationary measurements or they require rather sophisticated instrumentation. In general, they are not practical for in-line applications where virtually instantaneous species identification are required.

SUMMARY OF INVENTION

In accordance with this invention, a method and apparatus for non-contact and rapid species identification have been devised. The method and apparatus are derived from the fact that absorption of infra-red radiation by wood depends on type of species which is being irradiated. It has been experimentally demonstrated, that a relationship exists between the types of wood being irradiated with intense infra-red radiation and the density of surface modifications caused by this radiation. Furthermore, it has been determined, that the density of surface modifications can be translated into a quantitative measure by using an optical beam. An analyzed wood sample is irradiated with infra-red beams two (2) times: first with lower- and then with higher-energy density beam. The effects of these irradiations are analyzed with scanning optical beams. Intensities of the scattered optical beams are recorded by optical detector(s). It has been found, that various wood species may be identified by experimentally determining the following two (2) parameters:

$$SIP_1 = (I_{in} - I_1)/I_{in} \quad [1]$$

$$SIP_2 = (I_{in} - I_2)/I_{in} \quad [2]$$

where:

$SIP_1$ - Species Identification Parameter. The values of the parameter $SIP_1$ are predetermined experimentally for a preselected energy density $P_1$ of the infra-red radiation. The values of the $SIP_1$ are predetermined for all the range of the moisture content for given species;

$SIP_2$ - Species Identification Parameter. The values of the parameter $SIP_2$ are predetermined experimentally for a preselected energy density $P_2$ (such that $P_2 > P_1$) of the infra-red radiation. The values of the $SIP_2$ are predetermined for all the range of the moisture content for given species;

$I_{in}$ - is the intensity of optical radiation scattered from the analyzed portion of a substance surface prior to irradiation with the infra-red radiation.

$I_1$ - is the intensity of optical radiation scattered from the analyzed portion of a substance surface after it was irradiated with the infra-red radiation of the lower intensity ($P_1$);

$I_2$ - is the intensity of optical radiation scattered from the analyzed portion of a substance surface after it was irradiated with the infra-red radiation of the higher intensity ($P_2$);

It has been found that a set of the parameters $SIP_1$ and $SIP_2$ is the characteristic property of every type of wood and it can be used as the basis for the identification of various species. These parameters are also function of a moisture content. Therefore, they may be simultaneously used for the determination of the moisture content. The values of the SIPs are predetermined experimentally for all the range of moisture content of given species. These values are recorded and used as the calibration data.

The values of $P_1$ and $P_2$ are preselected energy densities of the infra-red radiation which is used in the measurements. These values are characteristic for a given apparatus. The values of $I_1$, $I_2$ and $I_{in}$ are measured by the optical detector(s) during the identification process.

The sequence of species identification is schematically illustrated in TABLE I. The $SIP_1$ and $SIP_2$ represent the species identification parameters. The various wood species are represented by the symbol $S_i$ (i.e. i=pine, balsam, spruce, etc.); the moisture content is represented by the symbol M. It has been experimentally demonstrated, that every set of SIP1 and SIP2 determines explicitly a given species and its moisture content.

The invented method allows for non-contact and rapid identification of various wood species. Also, the invented method allows for the simultaneous measurements of the moisture content. The identification of species and the moisture measurements can be done either for moving or stationary samples. The additional advantage of the method is that the apparatus can be placed at a distance from the analyzed substance because all the measurements may be carried out by low-divergence beams.

BRIEF DESCRIPTION OF THE DRAWINGS

FIG. 1 illustrates a schematic view of apparatus capable of identification of stationary samples. The apparatus includes an energy density adjustable infra-red source, a single source of optical radiation, and an optical detector.

FIG. 2 illustrates a schematic view of apparatus capable of identification of moving samples. The apparatus includes an energy density adjustable source of infra-red radiation, two sources of optical radiation, and two optical detectors.

FIG. 3 presents a graph plotting the species identification parameters $SIP_1$ and $SIP_2$ for lumber samples of spruce and balsam.

FIG. 4 presents a graph plotting the species identification parameters $SIP_1$ and $SIP_2$ for lumber samples of pine and balsam.

FIG. 5 presents a graph plotting the species identification parameters $SIP_1$ and $SIP_2$ for lumber samples of douglas-fir and balsam.

FIG. 6 presents a graph plotting the species identification parameters $SIP_1$ and $SIP_2$ versus moisture content for lumber samples of spruce and balsam.

FIG. 7 presents a graph plotting the species identification parameters $SIP_1$ and $SIP_2$ versus moisture content for lumber samples of pine and balsam.

FIG. 8 presents a graph plotting the species identification parameters $SIP_1$ and $SIP_2$ versus moisture content for lumber samples of douglas-fir and balsam.

DESCRIPTION OF PREFERRED EMBODIMENTS

Figure 1:
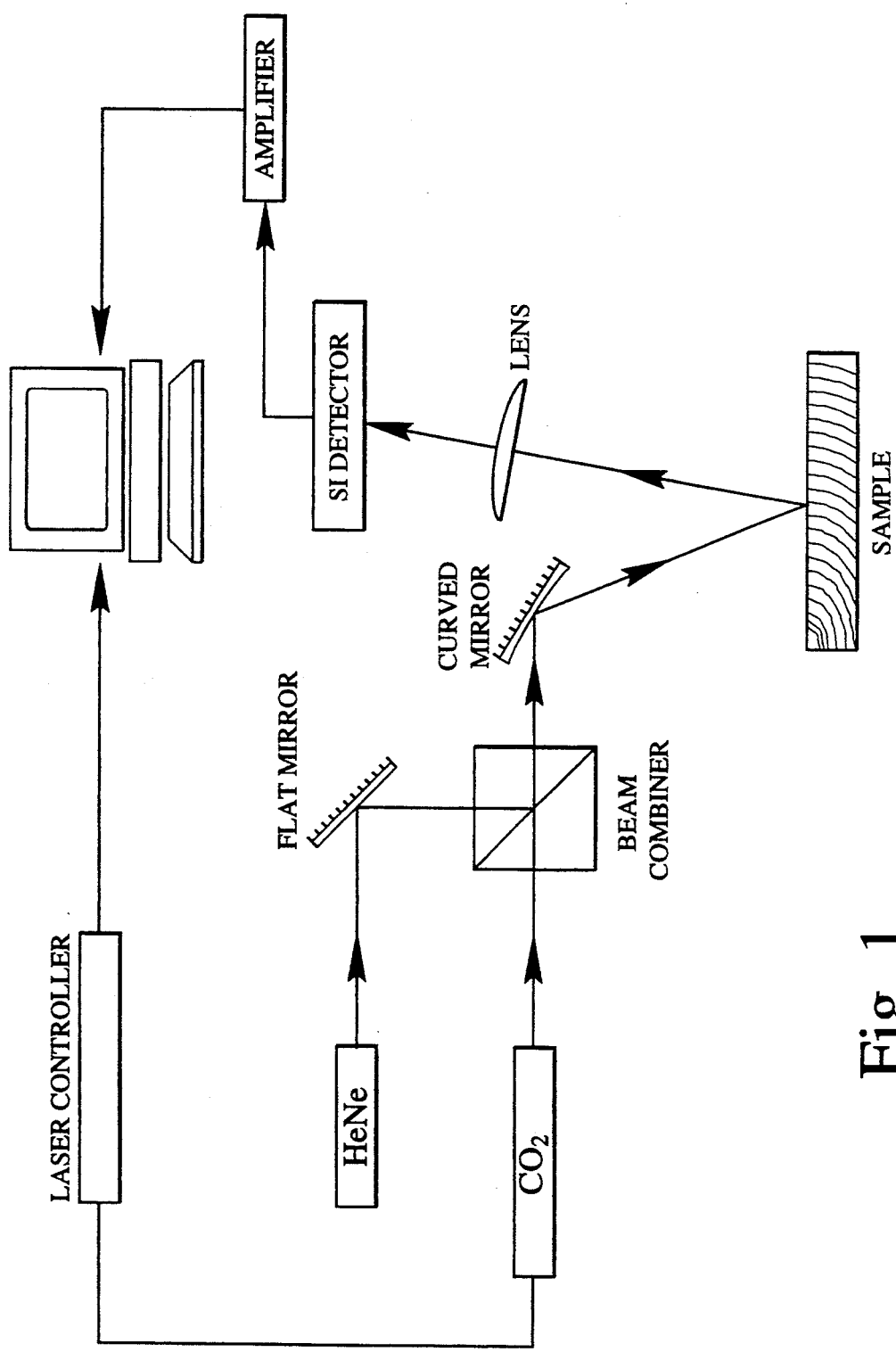
FIGS. 1 and 2 illustrate schematic views of two versions of the apparatus.

The apparatus embodiment illustrated in FIG. 1 is suitable for the species identification of stationary samples. A sample is first scanned with an analyzing optical beam from the source such as HeNe laser. The scattered optical radiation ($I_{in}$) is collected by the lens and recorded by the optical detector. This is followed by irradiating the sample surface with a lower energy density ($P_1$) infra-red beam from the $CO_2$ laser. The $CO_2$ laser beam is combined with the HeNe laser beam by using a ZnSe beam combiner. The $CO_2$ laser beam is focused on the sample by a curved mirror. The following step is to scan the sample surface again with the optical beam and to record the scattered intensity ($I_1$) by the optical detector. The next step is to irradiate the sample with a higher energy density ($P_2$) of the infra-red radiation from the $CO_2$ laser and to scan the surface again with the HeNe beam. The intensity ($I_2$) of scattered radiation is recorded by the detector. The arrangement of optical axes of the detector and the radiation sources is such that they converge at the sample surface. All the system components are controlled by a computer. The computer is equipped with a data aquisition board, which is used for data recording and analysis. The analyzed wood species are identified by calculating the parameters $SIP_1$ and $SIP_2$ according to the formulas [1,2] and then comparing their values with predetermined and recorded calibration data.

Figure 2:
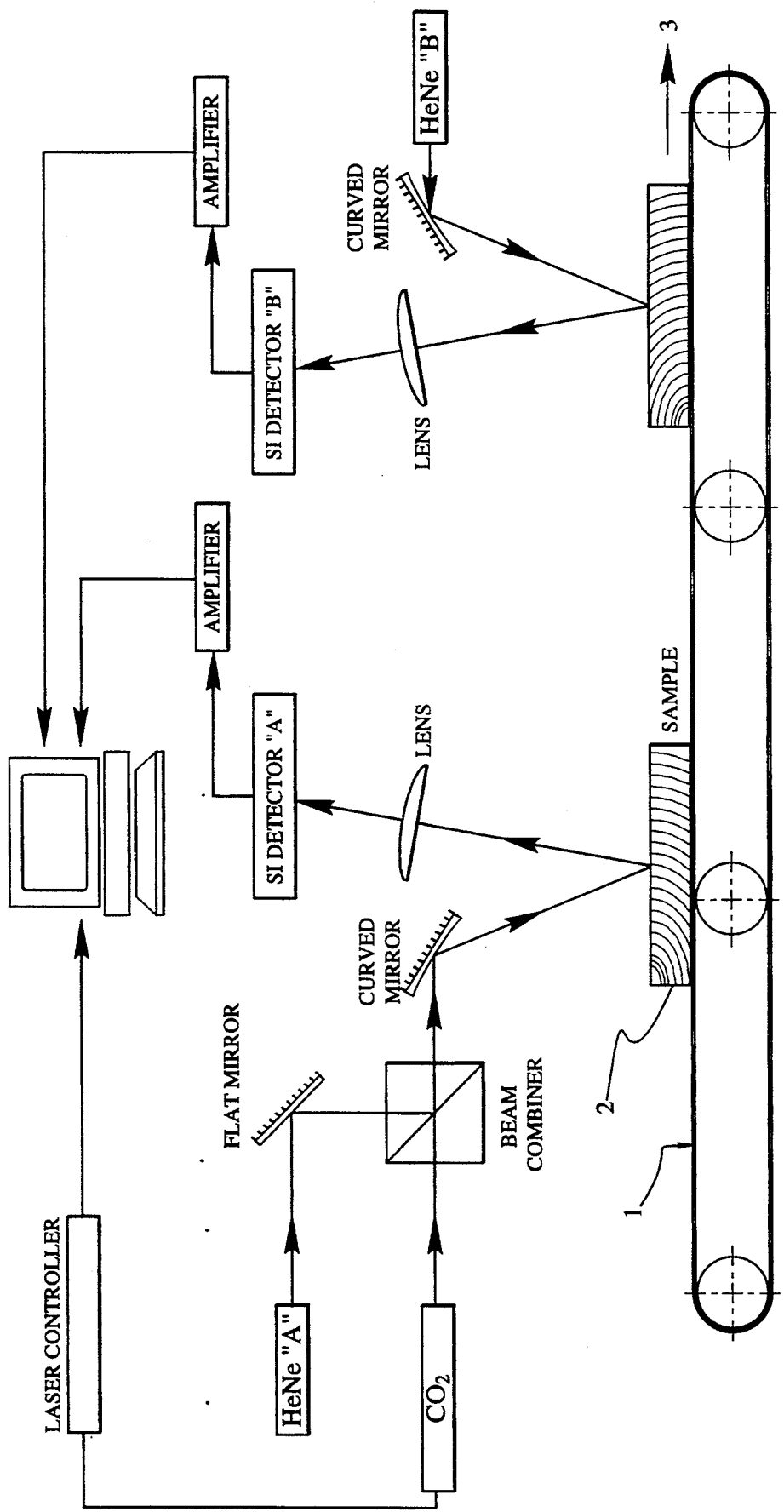

In the apparatus embodiment illustrated in FIG. 2, a conveyor 1 causes the sample 2 to move past the infra-red radiation from the $CO_2$ laser and the optical beams from the HeNe lasers "A" and "B". The scattered optical radiation ($I_{in}$, $I_1$ and $I_2$) are recorded by the optical detectors "A" and "B", respectively. The arrangement of optical axes of the radiation sources and the detectors is such, that they are in line with respect to the direction 3 in which the sample is being moved. The infra-red $CO_2$ laser irradiates the surface with two (2) pulses of an intense radiation of predetermined energy densities $P_1$ and $P_2$ (such that $P_2 > P_1$). This radiation causes the surface modifications. The modified portion of the surface is then scanned with the optical beam. The optical radiation scattered from the modified surface is recorded by the detector. All the system components are controlled by a computer. The computer is equipped with a data aquisition board, which is used for data recording and analysis. The sample is identified by comparing the calculated values of the parameters $SIP_1$ and $SIP_2$ with predetermined and recorded data.

In the following examples a $CO_2$ laser has been used as the source of infra-red radiation (MPB's model IN-70: wavelength 10.6 micron, 60 Watt output power, 7 mm beam diameter, pulsed at 50 msec). HeNe lasers have been used as the sources of the optical beams (Melles Gruiot's model 05LHP 991: wavelength 0.6328 micron, 10 mWatt output power, 0.7 mm beam diameter). The curved mirror (1 meter radius of curvature, 1 inch diameter) was used to focus the laser beam on the samples. The distance between the sample surface and the mirror was approximately 0.5 meter. The optical detectors used were manufactured by EG&G (Model 30809). The computer was equipped with a data acquisition board (a 12 bit analog-to-digital converter).

It has ben determined, that there is a linear relationship between the optimum intensity of the $CO_2$ laser beam and the speed of the conveyor. For example, the 60 Watt output power corresponds to the optimum speed of yhe conveyor of 120 feet per minute. Also, it has been determined, that the optimum value of higher intensity infra-red radiation (i.e. $P_2$) should be two (2) times higher than the $P_1$.

EXAMPLE I

Figure 3:
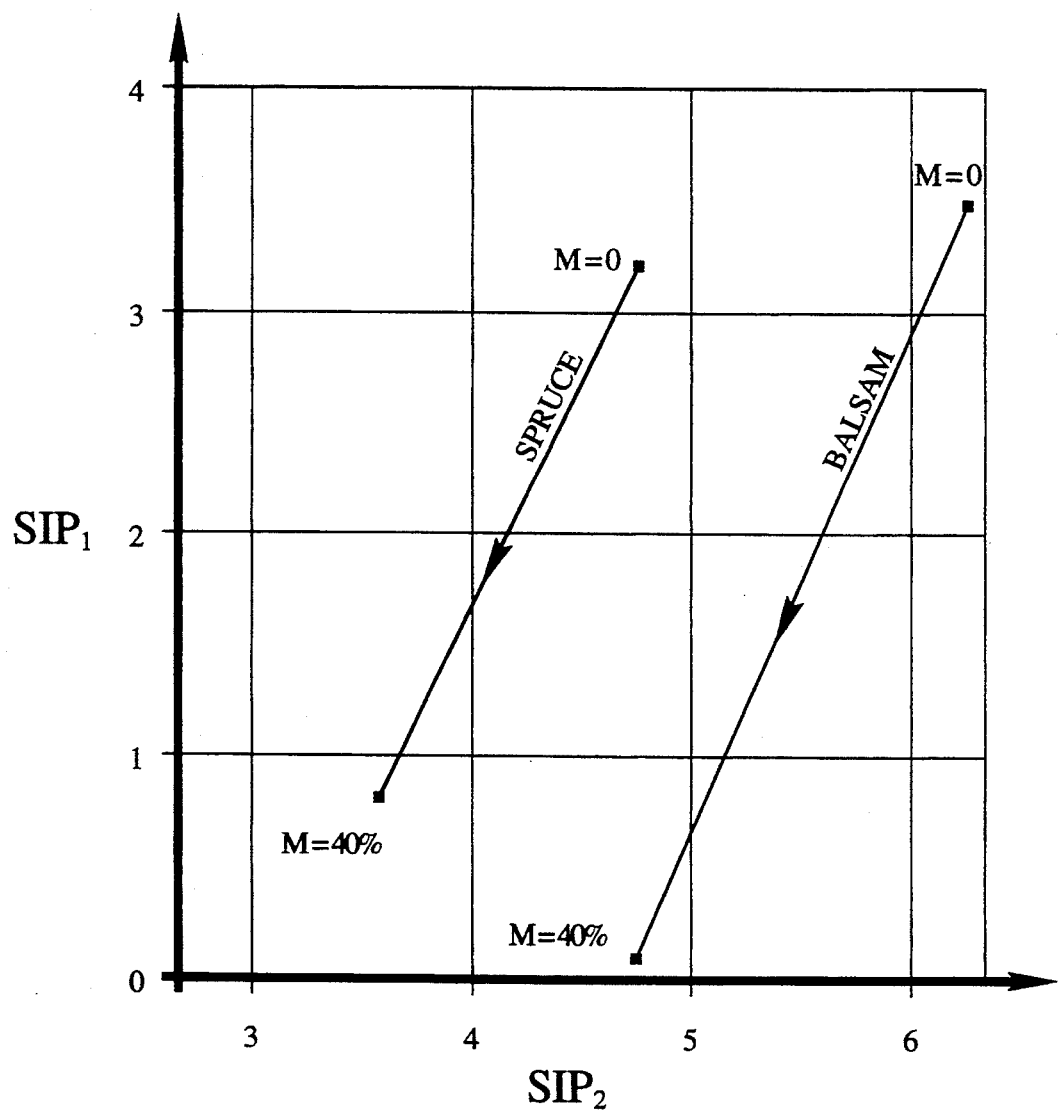
FIGS. 3-8 illustrate data obtained by using exemplary apparatus for species identification in accordance with this invention.
Figure 6:
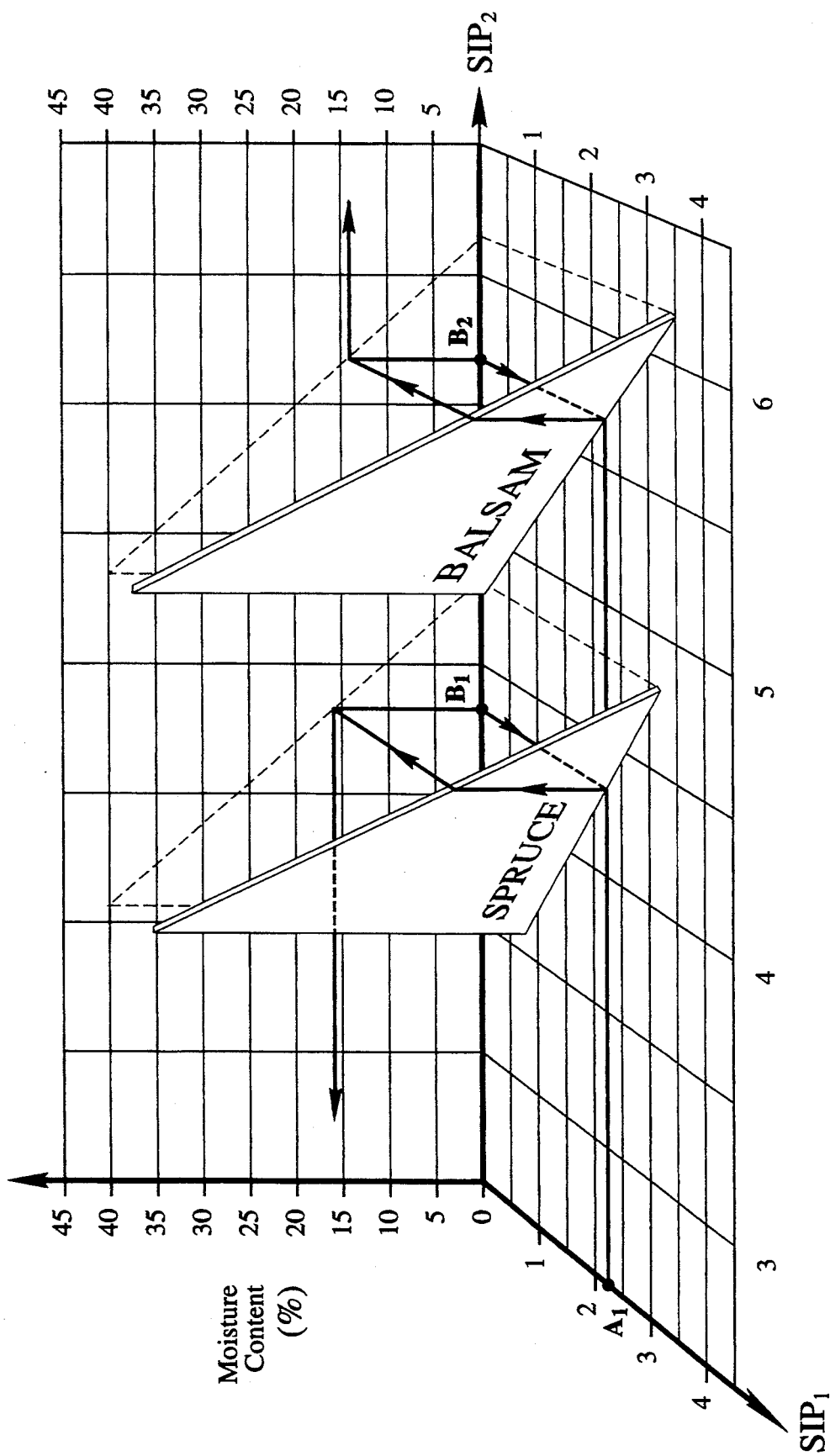

Pieces of two by four lumber spruce and balsam were analyzed with the described apparatus. All the analyzed samples contained various moisture content in the range from 0% to 40%. The samples were moving with the speed of 15 feet/minute. A $CO_2$ laser was used as the source of the infra-red radiation. The preselected values of the infra-red energy densities were: $I_1 = 0.02$ and $I_2 = 0.04$ [Joule/mm$^2$]. The graph of the species identification parameters $SIP_1$ and $SIP_2$ are plotted on FIG. 3. All the points along each of the plotted lines correspond to various moisture content for a given species. The arrows indicate moisture content gradient from 0% to 40%. FIG. 6 is a 3-dimensional representation of the species identification and moisture measurement calibration data for spruce and balsam.

The arrows on the FIG. 6 show the data interpretation sequence. For example, if the measured value of $SIP_1$ is 2.3 (i.e. point $A_1$); then there are two (2) possible corresponding values of $SIP_2$ i.e. $B_1$ and $B_2$. If the measured value of $SIP_2$ is in the range of 4.3, then it is explicit that the analyzed sample is spruce and its moisture content is in the range of 16%. If the measured value of $SIP_2$ is in the range of 5.7, then the analyzed sample is balsam and its moisture content is 14%.

EXAMPLE II

Figure 4:
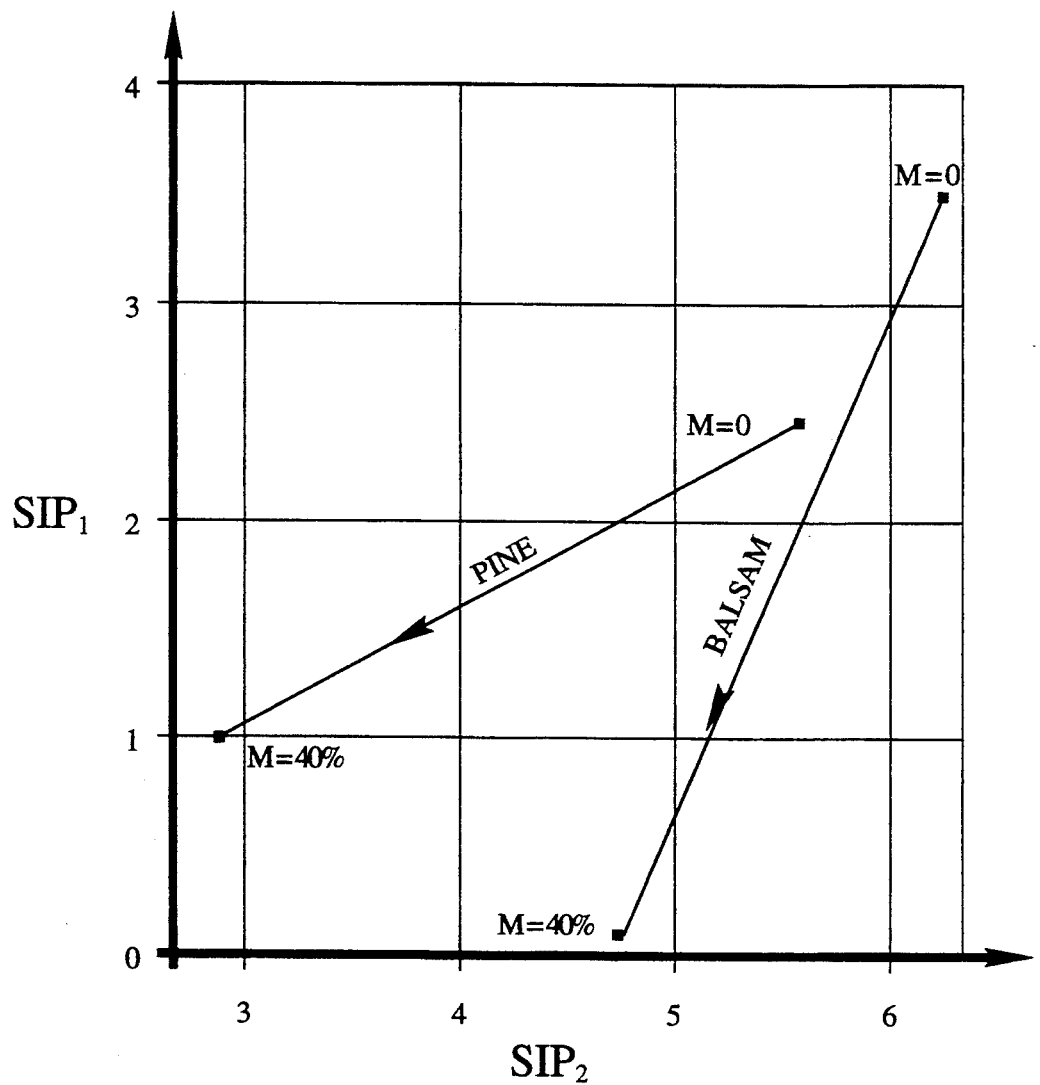
Figure 7:
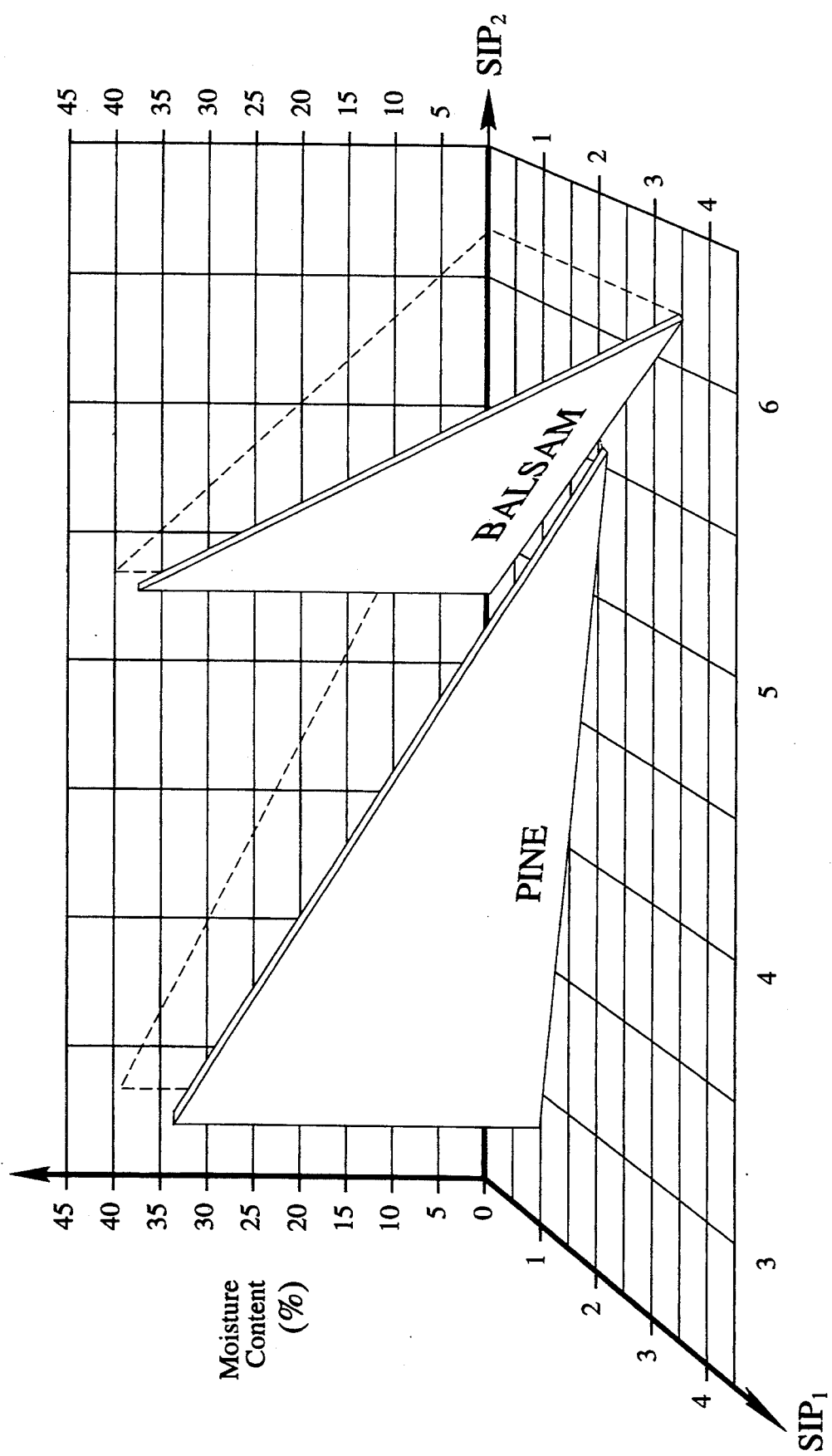

Pieces of two by four lumber pine and balsam were analyzed with the described apparatus. All the analyzed samples contained various moisture content in the range from 0% to 40%. The samples were moving with the speed of 15 feet/minute. A $CO_2$ laser was used as the source of the infra-red radiation. The preselected values of the infra-red energy densities were: $I_1 = 0.02$ and $I_2 = 0.04$ [Joule/mm$^2$]. The graph of the species identification parameters $SIP_1$ and $SIP_2$ are plotted on FIG. 4. All the points along each of the plotted lines correspond to various moisture content for a given species. The arrows indicate moisture content gradient from 0% to 40%. FIG. 7 is a 3-dimensional representation of the species identification and moisture measurement calibration data for pine and balsam.

EXAMPLE III

Figure 5:
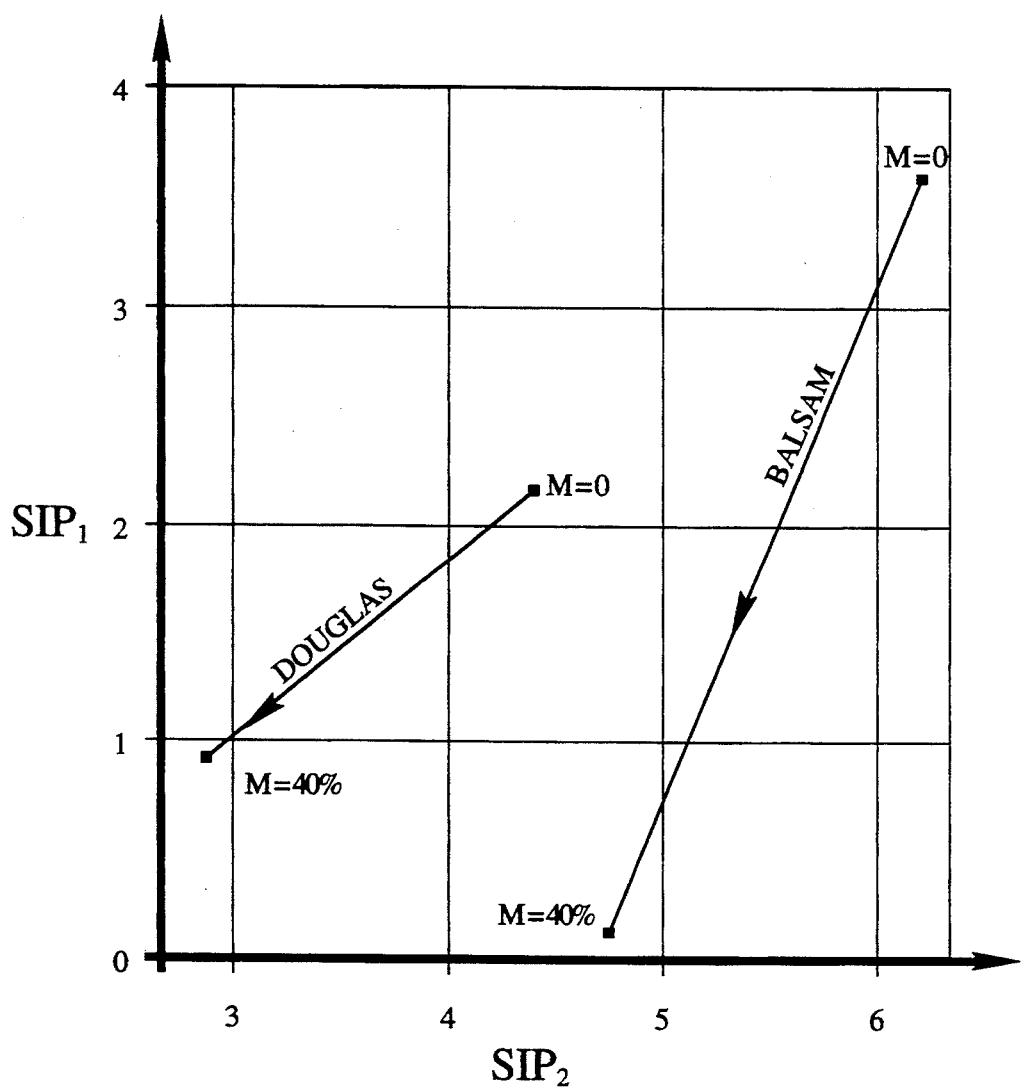
Figure 8:
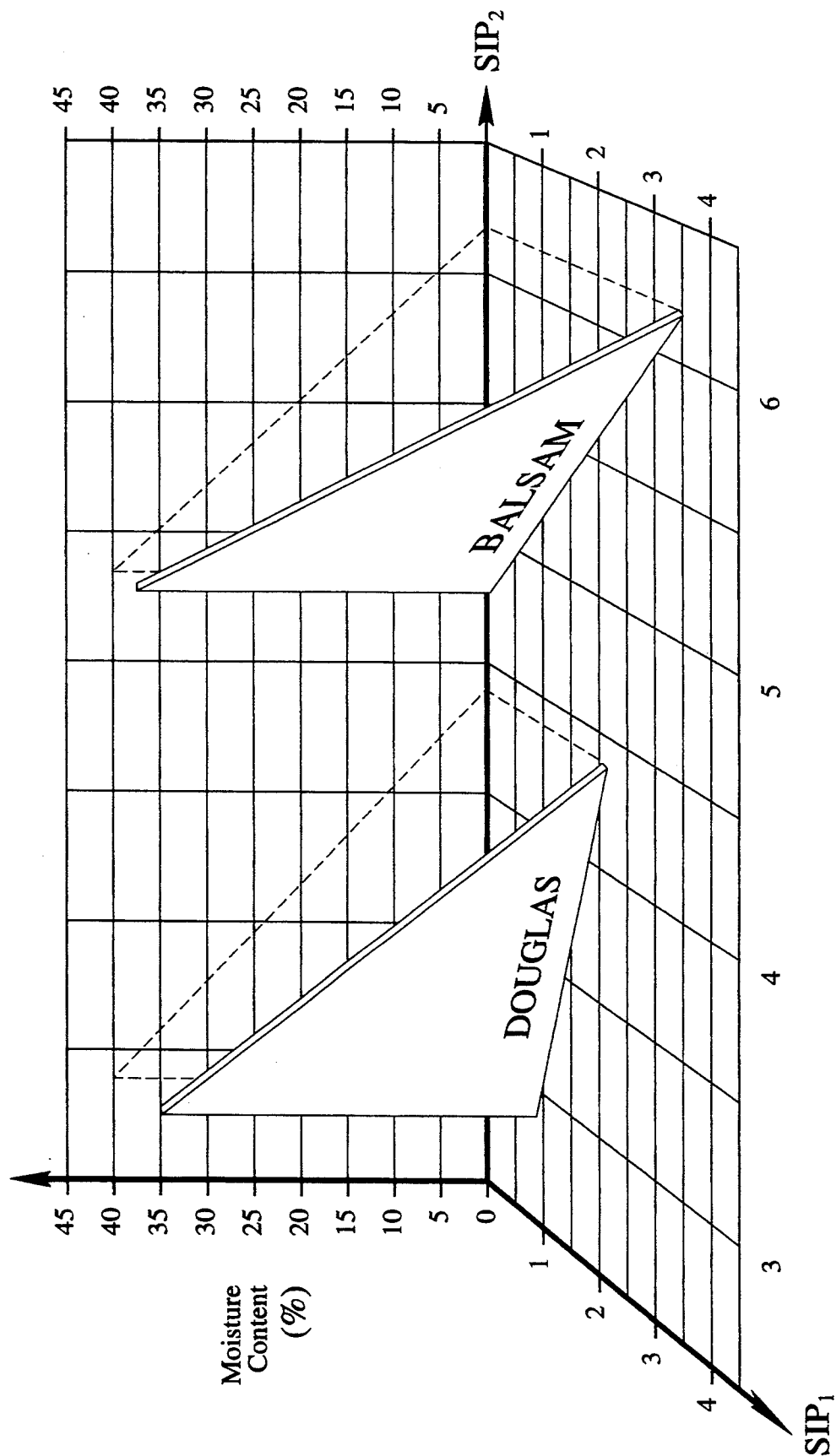

Pieces of two by four lumber douglas-fir and balsam were analyzed with the described apparatus. All the analyzed samples contained various moisture content in the range from 0% to 40%. The samples were moving with the speed of 15 feet/minute. A $CO_2$ laser was used as the source of the infra-red radiation. The preselected values of the infra-red energy densities were: $I_1 = 0.02$ and $I_2 = 0.04$ [Joule/mm$^2$]. The graph of the species identification parameters $SIP_1$ and $SIP_2$ are plotted on FIG. 5. All the points along each of the plotted lines correspond to various moisture content for a given species. The arrows indicate moisture content gradient from 0% to 40%. FIG. 8 is a 3-dimensional representation of the species identification and moisture measurement calibration data for douglas-fir and balsam.

We claim:

1. A method for the identification of wood species, said method comprising:

a) exposing a wood sample to be identified to an optical light beam of measuring predetermined energy density and measuring the intensity $I_{in}$ of the said optical light reflected from the sample;

b) irradiating an area of said wood sample with a laser beam of a first predetermined energy density level sufficient to permanently modify the microstructure of the said wood sample;

c) exposing the area irradiated with the laser beam of the first predetermined energy density level to an optical light beam of the measuring predetermined energy density and measuring the intensity $I_1$ of the said optical light reflected from the said area;

d) irradiating an area of the said wood sample with a laser beam of a second predetermined density level sufficient to permanently modify the microstructure of the said wood sample;

e) exposing the area irradiated with the laser beam of the second predetermined energy density level to an optical light beam of the measuring predetermined energy density and measuring the intensity $I_2$ of the optical light reflected from the said area; and f) identifying the said wood species by calculating the values $(I_{in}-I_1)/I_{in}$ and $(I_{in}-I_2)/I_{in}$ and comparing these values with the corresponding values for a known wood species.

2. A method for the identification of wood species, said method comprising:

a) exposing a wood sample to be identified to an optical light beam of measuring predetermined energy density and measuring the intensities $I_{in}$ of the optical light reflected from a plurality of preselected areas on the surface of the said wood sample;

b) irradiating each of the preselected areas of the said wood sample with a laser beam of a first predetermined energy density level sufficient to permanently modify the microstructure of the said wood sample;

c) exposing the said preselected areas irradiated with the laser beam of the first predetermined energy density level to an optical light beam of the measuring predetermined energy density and measuring intensities $I_1$ of the said optical light reflected from the said preselected areas;

d) irradiating each of the preselected areas of the said wood sample with a laser beam of a second predetermined energy density level sufficient to permanently modify the microstructure of the said wood sample;

e) exposing the preselected areas irradiated with the laser beam of the second predetermined energy density level to an optical light beam of the measuring predetermined energy density and measuring intensities $I_2$ of the optical light reflected from the preselected areas; and f) identifying the said wood species by calculating the values $(I_{in}-I_1)/I_{in}$ and $(I_{in}-I_2)/I_{in}$ and comparing these values with the corresponding values for a known wood species.

3. A method for the identification of wood species comprising:

a) measuring intensity $I_{in}$ of optical radiation of measuring predetermined energy density scattered from a selected area on the surface of a wood sample;

b) permanently modifying the selected area on the surface of the said wood sample by irradiating it with infra-red radiant energy of a first predetermined energy density level;

c) measuring intensity $I_1$ of optical radiation of the measuring predetermined energy density scattered from the area modified with infra-red radiant energy of the first predetermined energy density level;

d) permanently modifying the selected area on the surface of the said wood sample by irradiating it with infra-red radiant energy of a second predetermined energy density level;

e) measuring intensity $I_2$ of said optical radiation of the measuring predetermined energy density scattered from the area modified with infra-red radiant energy of the second predetermined energy density level; and f) identifying the wood species by calculating the values of $(I_{in}-I_1)/I_{in}$ and $(I_{in}-I_2)/I_{in}$ and comparing these values with the corresponding values for a known wood species.

4. A method as claimed in claim 3, wherein the said wood sample moves at a speed relative to radiant energy sources.

5. A method for the identification of the type of wood species comprising:

a) measuring intensities $I_{in}$ of optical radiation of measuring predetermined energy density scattered from a plurality of preselected areas on the surface of a wood sample;

b) permanently modifying each of the preselected areas of the said wood sample by irradiating them with infra-red radiant energy of a first predetermined energy density level;

c) measuring intensities $I_1$ of optical radiation of the measuring predetermined energy density scattered from the preselected areas modified with infra-red radiant energy of the first predetermined energy density level;

d) permanently modifying each of the preselected areas of the said wood sample by irradiating them with infra-red radiant energy of a second predetermined energy density level;

e) measuring intensities $I_2$ of optical radiation of the measuring predetermined energy density scattered from the preselected areas modified with infra-red radiant energy of the second predetermined energy density level; and f) identifying the type of species by calculating the values of $(I_{in}-I_1)/I_{in}$ and $(I_{in}-I_2)/I_{in}$ and comparing these values with the corresponding values for known types of wood species.

6. A method as claimed in claim 5, wherein for each preselected surface area steps a), b), c), d), e) and f) are carried out simultaneously.

7. A method as claimed in claim 5, wherein the said wood sample moves at a speed relative to radiant energy sources.

8. A method as claimed in claim 6, wherein the said wood sample moves at a speed relative to radiant energy sources.

9. A method for simultaneous identification and determination of the moisture content of a wood sample comprising:

a) measuring intensity $I_{in}$ of optical radiation of measuring predetermined energy density scattered from a selected area on the surface of the wood sample;

b) permanently modifying the selected area on the surface of the said wood sample by irradiating it with infra-red radiant energy of a first predetermined energy density level;

c) measuring intensity $I_1$ of optical radiation of the measuring predetermined energy density scattered from the area modified with infra-red radiant energy of the first predetermined energy density level;

d) permanently modifying the selected area of the said wood sample by irradiating it with infra-red radiant energy of a second predetermined energy density level;

e) measuring intensity $I_2$ of optical radiation of the measuring predetermined energy density scattered from the area modified with infra-red radiant energy of the second predetermined energy density level; and f) identifying the species and simultaneously determining the moisture content of the said wood sample by calculating the values $(I_{in}-I_1)/I_{in}$ and $(I_{in}-I_2)/I_{in}$ and comparing these values with the corresponding values for a known wood species.

10. The method as claimed in claim 9, wherein the said wood sample moves at a speed relative to radiant energy sources.

11. A method for the simultaneous determination of the moisture content and identifying the type of species of a wood sample comprising:

a) measuring intensities $I_{in}$ of optical radiation of measuring predetermined energy density scattered from a plurality of preselected areas on the surface of the wood sample;

b) permanently modifying each of the preselected areas of the said wood sample by irradiating them with infra-red radiant energy of a first predetermined energy density level;

c) measuring intensities $I_1$ of optical radiation of the measuring predetermined energy density scattered from the preselected areas modified with infra-red radiant energy of the first predetermined energy density level;

d) permanently modifying each of the preselected areas of the said wood sample by irradiating them with infra-red radiant energy of a second predetermined energy density level;

e) measuring intensities $I_2$ of optical radiation of the measuring predetermined energy density scattered from the preselected areas modified with infra-red radiant energy of the second predetermined energy density level; and f) identifying the type of species and simultaneously determining the moisture content of the wood sample by calculating the values of $(I_{in}-I_1)/I_{in}$ and $(I_{in}-I_2)/I_{in}$ and comparing these values with the corresponding values for known types of wood species.

12. A method as claimed in claim 11, wherein for each preselected surface area steps a), b), c), d), e) and f) are carried out simultaneously.

13. The method as claimed in claim 11, wherein the said wood sample moves at a speed relative to radiant energy sources.

14. The method as claimed in claim 12, wherein the said wood sample moves at a speed relative to radiant energy sources.

15. An apparatus for the non-contact identification of a wood species sample, said apparatus comprising in combination:
- an optical light source for subjecting said wood species sample to measuring optical light;
- an optical detector positioned relative to said optical light source to measure the intensity of optical light reflected by said wood species sample after exposing said wood species sample to the measuring optical light;
- an infra-red source to irradiate said wood species sample on a selected area of said sample at two predetermined energy density levels sufficient to permanently modify the microstructure of said wood species sample and
- means to actuate the said optical light source and detector, to measure the intensity of optical light reflected by said wood species sample after having been exposed to the measuring optical light, and to measure the intensity of optical light reflected by said selected area of said wood species sample after having been irradiated with said infra-red source.

* * * * *